US007465831B2

(12) United States Patent
Merli et al.

(10) Patent No.: US 7,465,831 B2
(45) Date of Patent: Dec. 16, 2008

(54) LEVALBUTEROL HYDROCHLORIDE POLYMORPH A

(75) Inventors: Valeriano Merli, Lecco (IT); Silvia Mantovani, Milan (IT); Stefano Bianchi, Como (IT); Paola Daverio, Milan (IT); Angelo Spreafico, Lecco (IT); Judith Aronhime, Rehovot (IL); Adrienne Kovacsne-Mezei, Debrecen (HU)

(73) Assignee: Teva Pharmaceutical Fine Chemicals s.r.l., Bulciago (LC) (IT)

( * ) Notice: Subject to any disclaimer, the term of this patent is extended or adjusted under 35 U.S.C. 154(b) by 0 days.

(21) Appl. No.: 11/827,481

(22) Filed: Jul. 11, 2007

(65) Prior Publication Data

US 2008/0021244 A1 Jan. 24, 2008

Related U.S. Application Data

(63) Continuation of application No. 11/133,720, filed on May 20, 2005, now abandoned.

(60) Provisional application No. 60/573,025, filed on May 20, 2004, provisional application No. 60/577,979, filed on Jun. 7, 2004, provisional application No. 60/646,803, filed on Jan. 25, 2005, provisional application No. 60/577,819, filed on Jun. 7, 2004, provisional application No. 60/583,777, filed on Jun. 28, 2004, provisional application No. 60/583,642, filed on Jun. 28, 2004, provisional application No. 60/587,673, filed on Jul. 13, 2004, provisional application No. 60/632,625, filed on Dec. 2, 2004.

(51) Int. Cl.
*C07C 213/08* (2006.01)
*C07C 213/10* (2006.01)

(52) U.S. Cl. ...................................................... 564/365

(58) Field of Classification Search ....................... None
See application file for complete search history.

(56) References Cited

U.S. PATENT DOCUMENTS 5,399,765 A 3/1995 Gao et al.
5,442,118 A 8/1995 Gao et al.
6,365,756 B1 4/2002 Stevens et al.

FOREIGN PATENT DOCUMENTS

| | | |
|---|---|---|
| AU | B-25559/95 | 12/1995 |
| CA | 1 040 658 | 10/1978 |
| CA | 2 190 577 | 11/1995 |
| CA | 2 320 756 | 8/1999 |
| CN | 1273966 A | 11/2000 |
| CN | 1382685 | 12/2002 |
| GB | 1 298 494 | 12/1972 |
| GB | 1298494 | 12/1972 |
| WO | WO 92/04314 | 3/1992 |
| WO | WO 95/29146 | 11/1995 |
| WO | WO 95/32178 | 11/1995 |
| WO | WO 99/42460 | 8/1999 |
| WO | WO 02/48090 A1 | 6/2002 |
| ZA | 990977 | 4/2000 |

OTHER PUBLICATIONS

"Briefing: Levalbuterol Hydrochloride; Levalbuterol Inhalation Solution" 2006 USPC, Inc. 33(1) In-Process Revision: Levalbuterol Hydrochloride http://www.usppf.com/pf/pub/data/v331/MON_IPR_331_m44602.xml, pp. 1-6.

Handley, D.A., et al., "Levalbuterol hydrochloride", Exp. Opin. Invest. Drugs, 1998, 7(12), pp. 2027-2041.

Halabi, A., et al., "Validation of a chiral HPLC assay for (*R*)-salbutamol sulfate", Journal of Pharmaceutical and Biomedical Analysis, 2004, 34, pp. 45-51,.

Ferrayoli, C.G., et al., "Resolution of Racemic Albuterol Via Diastereomeric Salts Formation with Di-*p*-Toluoyl-D-Tartaric Acid", Enantiomer, 2000, 5, pp. 289-291.

Caira, M.R., "Crystalline Polymorphism of Organic Compounds", Topics in Current Chemistry, 1998, 198, pp. 163-208.

*Primary Examiner*—Brian J Davis
(74) *Attorney, Agent, or Firm*—Kenyon & Kenyon LLP

(57) ABSTRACT

The invention is directed to processes for making levalbuterol HCl Polymorph A from by suspending or forming a first slurry of (R)-SLB(D)-DBTA in at least a first organic solvent, adding HCl to the suspension or slurry of the solid (R)-SLB.D-DBTA until the (R)-SLB.D-DBTA forms levalbuterol HCl Polymorph A, and isolating the levalbuterol HCl Polymorph A.

12 Claims, 1 Drawing Sheet

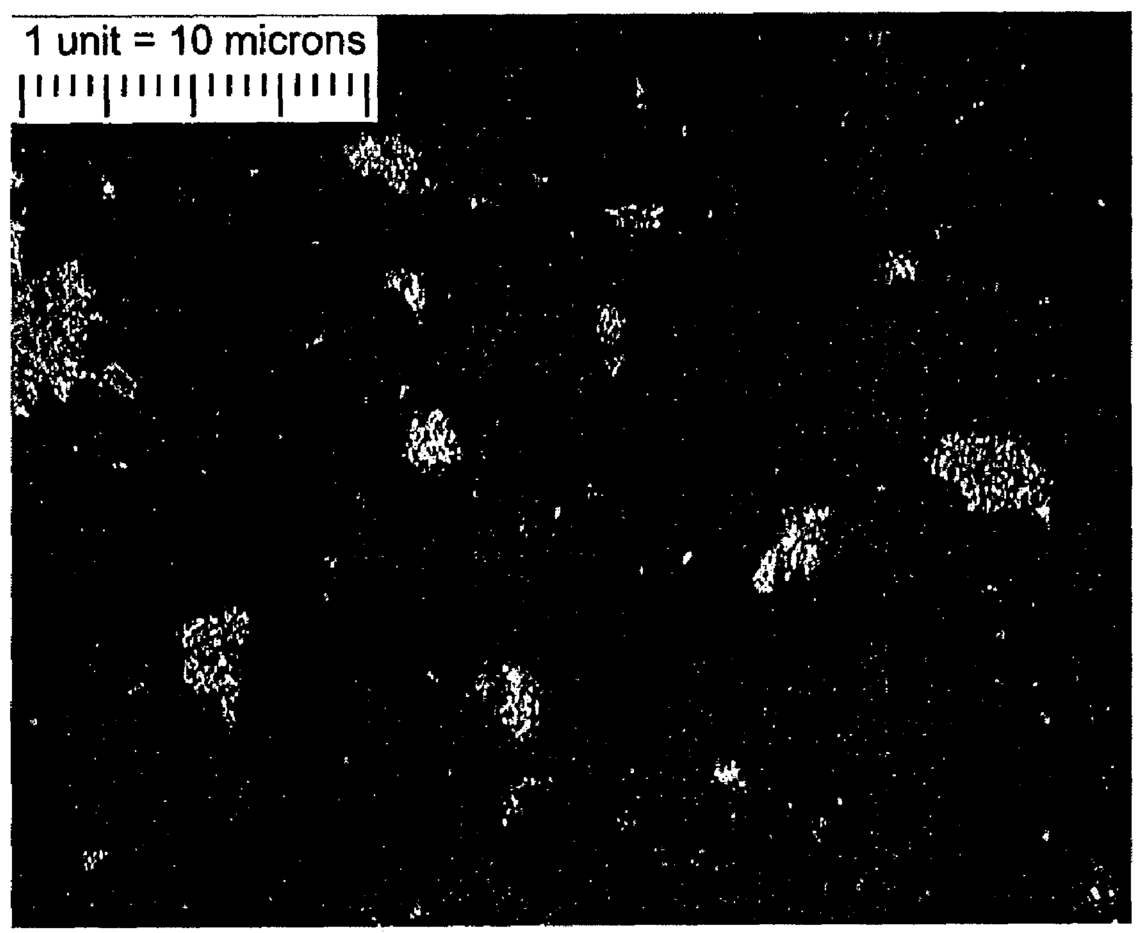
1 unit = 10 microns

LEVALBUTEROL HYDROCHLORIDE POLYMORPH A

CROSS-REFERENCE TO RELATED APPLICATIONS

This application is a continuation of U.S. application Ser. No. 11/133,720, now abandoned, filed on May 20, 2005, which claims the benefits of U.S. Provisional Patent Application Nos. 60/573,025, filed May 20, 2004, 60/577,979, filed Jun. 7, 2004, 60/646,803, filed Jan. 25, 2005, 60/577,819, filed Jun. 7, 2004, 60/583,777, filed Jun. 28, 2004, 60/583,642, filed Jun. 28, 2004, 60/587,673, filed Jul. 13, 2004 and 60/632,625, filed Dec. 2, 2004, the contents of all of which are incorporated herein by reference.

FIELD OF THE INVENTION

The present invention encompasses processes for the preparation of levalbuterol hydrochloride Polymorph A and to pure forms thereof.

BACKGROUND OF THE INVENTION

Activation of $\beta_2$-adrenergic receptors on airway smooth muscle leads to the activation of adenylcyclase and to an increase in the intracellular concentration of cyclic-3',5'-adenosine monophosphate (cyclic AMP). This increase in cyclic AMP leads to the activation of protein kinase A, which inhibits the phosphorylation of myosin and lowers intracellular ionic calcium concentrations, resulting in relaxation. Levalbuterol relaxes the smooth muscles of the airways from the trachea to the terminal bronchioles. Levalbuterol acts as a functional antagonist to relax the airway irrespective of the spasmogen involved, thus protecting against all bronchoconstrictor challenges. Increased cyclic AMP concentrations are also associated with the inhibition of release of mediators from mast cells in the airway. The chemical name for levalbuterol HCl is (R)-$\alpha^1$-[[(1,1-dimethylethyl)amino]methyl]-4-hydroxy-1,3-benzenedimethanol hydrochloride.

Levalbuterol HCl has been synthesized using a variety of synthetic schemes. For example, Great Britain patent No. 1298494 discloses synthesizing levalbuterol first by crystallizing the alkyl acetate of the 4-carboxylate derivative (Formula 1) using ditolyltartaric acid and isolating the selected crystalline fraction.

Formula 1

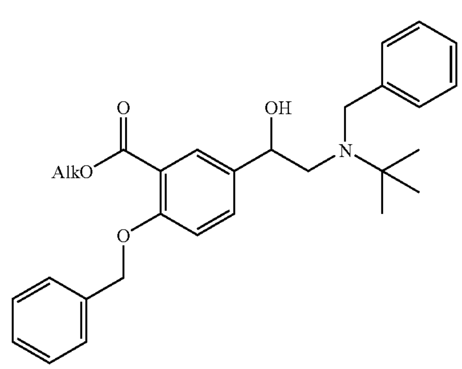

Thereafter, the crystal undergoes debenzylation deprotection, followed by ester reduction to yield levalbuterol.

Chinese patent No. 1,273,966, the salt of (R)-albuterol D-dibenzoyltartaric acid is treated with potassium carbonate in water and an organic solvent, such as ethylacetate. After phase separation and extraction of the aqueous layer, the collected organic layer is dried and levalbuterol free base crystallizes overnight. The crystalline levalbuterol free base is dissolved in anhydrous alcohol, followed by addition of HCl to obtain crystalline levalbuterol HCl. Also, levalbuterol HCl is synthesized by acid displacement from (R)-albuterol D-dibenzoyltartaric acid salt dissolved in acetone and the addition of an ether solution of HCl.

Despite the many attempts of the prior art to synthesize pure levalbuterol, still novel synthetic processes of preparing polymorphically pure levalbuterol are needed to reduce the steps necessary for synthesis.

SUMMARY OF THE INVENTION

The invention encompasses processes for making levalbuterol HCl Polymorph A comprising suspending or forming a first slurry of (R)-SLB(D)-DBTA (((R)(−)$\alpha^1$-[[(1,1-dimethylethyl)amino]methyl]-4-hydroxy-1,3-benzenedimethanol(D)-dibenzo-yltartrate) in at least a first organic solvent; adding HCl to the suspension or slurry of the solid (R)-SLB(D)DBTA until the (R)-SLB(D)-DBTA forms pure levalbuterol HCl Polymorph A; and isolating the pure levalbuterol HCl Polymorph A. The first solvent may be at least one linear or branched $C_3$-$C_{10}$ ester, linear or branched $C_3$-$C_{10}$ ketone, linear or branched $C_3$-$C_{10}$ ether, $C_6$-$C_{10}$ aromatic hydrocarbon, linear or branched $C_1$-$C_4$ alcohol, dimethylsulfoxide, dimethylformamide, methylene chloride, or acetonitrile. Preferably, the first solvent is at least one of ethyl acetate, tetrahydrofuran, dimethylcarbonate, acetonitrile, toluene, methanol, dimethylsulfoxide, or dimethylformamide.

Preferably, the process further comprises chemical purification of the pure levalbuterol HCl Polymorph A by suspending or forming a second slurry of the pure levalbuterol HCl Polymorph A in a second solvent; and isolating the pure levalbuterol HCl Polymorph A. Preferably, the second solvent comprises 95% ethylacetate and about 5% methanol by volume.

The invention also encompasses processes for making pure levalbuterol HCl Polymorph A by the conversion of levalbuterol HCl Polymorph B into pure levalbuterol Polymorph A comprising forming a slurry or suspension of levalbuterol HCl Polymorph B with a first organic solvent mixture as described above; and isolating pure levalbuterol Polymorph A from the slurry or suspension.

The invention also encompasses levalbuterol HCl polymorph A having levalbuterol HCl Polymorph B in an amount of not more than about 5% by weight. Preferably, the levalbuterol HCl Polymorph A has levalbuterol HCl Polymorph B present in an amount of not more than 3%, and more preferably, in an amount of not more than 1% by weight.

BRIEF DESCRIPTION OF THE FIGURES

FIG. 1 illustrates levalbuterol HCl Polymorph A in a crystalline particle size having a maximum particle size of about 150 microns.

DETAILED DESCRIPTION OF THE INVENTION

The present invention relates to the solid state physical properties of levalbuterol HCl. These properties can be influenced by controlling the conditions under which levalbuterol HCl is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. These conformational and orientational factors in turn result in particular intramolecular interactions and intermolecular interactions with adjacent molecules that influence the macroscopic properties of the bulk compound. A particular polymorphic form may give rise to distinct spectroscopic properties that may be detectable by powder X-ray diffraction, solid state 13C NMR spectrometry and infrared spectrometry. The polymorphic form may also give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others.

As used herein, the term: "(R)-SLB(D)-DBTA" refers to R enantiomer of albuterol D-DBTA complex.

Polymorph A may be characterized either by x-ray diffraction (XRD); infrared spectroscopy; or by differential scanning calorimetry (DSC). Polymorph A is characterized using x-ray diffraction by peaks at 10.7, 15.3, 15.6, 19.1, and 23.9 degree two-theta, ±0.2 two-theta. Polymorph A may be further characterized using x-ray diffraction peaks at 6.9, 20.7, 27.4, and 32.4 degree two-theta, ±0.2 two-theta. Alternatively, Polymorph A is characterized by infrared peaks at 3534, 3414, 3087, 1437, 1304, and 1087 $cm^{-1}$. Polymorph A may be further characterized by IR peaks at 2979, 2797, 1613, 1547, 1505, 1481, 1397, 1365, 1325, 1243, 1199, 1152, 1109, 1076, 1056, 1030, 990, 920, 839, 792, and 640 $cm^{-1}$. Polymorph A is characterized by DSC data having one endothermic peak due to melting at about 171° C. to 193° C. Polymorph A is also characterized by a Loss On Drying (L.O.D.) of about 0.09% to 1.2% or a water content of 0.09 to 0.3% by weight.

The amount of levalbuterol HCl Polymorph B present in the Polymorph A can easily be determined by comparing the characteristic peak at 8.7 degree two-theta in an X-ray diffraction pattern. As used herein, the term "pure levalbuterol HCl Polymorph A" refers to levalbuterol HCl Polymorph A having levalbuterol HCl Polymorph B in an amount less than about 5% by weight. Preferably, the levalbuterol HCl Polymorph A does not contain more than 3% of levalbuterol HCl Polymorph B, and most preferably not more than 1% by weight.

The invention encompasses processes for preparing levalbuterol Polymorph A with considerable simplicity. The process for preparing pure levalbuterol Polymorph A comprises suspending or forming a first slurry of the R enantiomer of albuterol D-DBTA complex ("(R)-SLB.D-DBTA") in a first organic solvent; adding HCl to the suspension of the solid (R)-SLB.D-DBTA until the (R)-SLB.D-DBTA forms pure levalbuterol HCl Polymorph A; and isolating the pure levalbuterol HCl Polymorph A. Not to be limited by theory, it is believed that the process occurs by a solid to solid transformation.

The first solvent includes, but is not limited to, at least one linear or branched $C_3$-$C_{10}$ ester, linear or branched $C_3$-$C_{10}$ ketone, linear or branched $C_3$-$C_{10}$ ether, $C_6$-$C_{10}$ aromatic hydrocarbon, linear or branched $C_1$-$C_4$ alcohol, dimethylsulfoxide, dimethylformamide, methylene chloride, or acetonitrile. Optionally, the first solvent includes water. Preferably, the first solvent includes, but is not limited to, at least one of ethylacetate, tetrahydrofuran, dimethylcarbonate, acetonitrile, toluene, methanol, dimethylsulfoxide, or dimethylforamide. When the first solvent comprises two solvents, one solvent is present in about 70% and the other solvent is present in about 30% by volume. Preferably, the first solvent comprises ethylacetate present in an amount of about 70% to 100% and methanol present in an amount of about 1% to 30% by volume. More preferably, the first solvent comprises ethylacetate:methanol in a ratio of about 90 to about 10 by volume, and most preferably, in a ratio of 95:5 by volume.

The suspension or slurry may be carried out at temperatures of about −10° C. to about 40° C., more preferably at about room temperature.

The HCl may be added as a solution or a gas. For example, methods for adding HCl include, but are not limited to, adding aqueous HCl (37%), HCl gas, HCl in DMF, or HCl in ethereal solutions. Typically, HCl is added in an amount of about 1.2 equivalents of HCl per equivalent of (R)-SLB.D-DBTA.

The first suspension or slurry may be cooled, preferably at a temperature of about −10° C. to about 10° C., more preferably at about −5° C. to about 5° C., and most preferably at a about −2° C. to about 2° C.

Formation of pure levalbuterol polymorph A of the invention is dependent upon the solvent(s) of the first suspension or slurrying. Table 1 summarizes the solvents used to obtain pure levalbuterol HCl Polymorph A.

TABLE 1

Results of Different Reaction and Slurry Solvents

| Sample | Solvents | Crystal Form | DSC peak (° C.) | DSC Enthalpy (J/g) |
|---|---|---|---|---|
| 1 | EtOAc-DMF (90:10) | A | | 182 (118) |
| 2 | EtOAc-MeOH (90:10) | A | | 175 (123) |

TABLE 1-continued

Results of Different Reaction and Slurry Solvents

| | | | DSC | |
|---|---|---|---|---|
| Sample | Solvents | Crystal Form | peak (° C.) | Enthalpy (J/g) |
| 3 | Acetone-$H_2O$ (95:5, 0° C.) | A | | 190 (165) |
| 4 | EtOAc | A | | 171 (127) |
| 5 | $CH_3CN$ | A | | 179 (141) |
| 6 | IPA (filtered at 0-2° C.) | A | | 187 (128) |
| 7 | EtOAc-MeOH (90:10), HCl | A | | 191 (92), 192 (47) |
| 8 | Acetonitrile | A | | 189 (157) |
| 9 | Acetonitrile | A | | 188 (131) |
| 10 | EtOAc-DMF (90:10) | A | | 181 (116) |
| 11 | EtOAc-DMF (90:10) | A | | 188 (130) |
| 12 | EtOAc-DMF (90:10) | A | | 184 (150) |
| 13 | EtOAc-DMF (90:10) | A | | 189 (108) |
| 14 | EtOAc-MeOH (90:10) | A | | 189 (153) |
| 15 | EtOAc-MeOH (95:5, 1-6 volumes) | A | | 193 (163) |
| 16 | EtOAc-MeOH (95:5) | A | | 185 (158) |
| 17 | EtOAc-MeOH (95:5) | A | | 182 (134) |
| 18 | EtOAc-MeOH (90:10) | A | | 193 (163) |
| 19 | EtOAc-MeOH (90:10) | A | | 193 (160) |
| 20 | EtOAc-MeOH (90:10) | A | | 189 (142) |
| 21 | EtOAc-MeOH (90:10), HCl (5% MeOH) | A | | 181 (121) |
| 22 | EtOAc-MeOH (90:10) | A | | 183 (153) |
| 23 | EtOAc-MeOH (95:5) | A | | 191 (130) |
| 24 | Acetone | A | | 194 (138) |
| 25 | Toluene | A | | 190 (140) |
| 26 | EtOAc-MeOH (90:10) | A | | 193 (125) |
| 27 | Isopropyl ether | A | | 193 (122) |
| 28 | EtOAc-MeOH (95:5) | A | | 190 (119) |
| 29 | EtOAc-MeOH (95:5) | A | | 189 (129) |
| 30 | Dichloromethane | A | | 193 (112) |
| 31 | Acetonitrile | A | | 194 (118) |
| 32 | methyl tert-butyl ether (MTBE) | A | | 193 (117) |
| 33 | BuOAc | A | | 194 (137) |
| 34 | Isopropanol | A | | 194 (130) |

The presence of the polymorph was determined by XRD and a Differential Scanning Calorimetry (DSC) for each was taken. Based on DSC curves of levalbuterol HCl, Polymorph A exhibits one endothermic peak due to melting. Due to decomposition during melting, a melting range of about 171° C. to about 194° C. was determined for Polymorph A.

Optionally, the process further comprises chemical purification levalbuterol HCl Polymorph A by suspending or forming a second slurry of the levalbuterol HCl Polymorph A in a second solvent; and isolating pure levalbuterol HCl Polymorph A. As used herein, the term "chemical purification" refers to the separation of residual traces of D-DBTA from the levalbuterol HCl, by a slurry or suspension.

The second solvent includes, but is not limited to, at least one linear $C_3$-$C_5$ ester, $C_6$-$C_7$ aromatic hydrocarbon, $C_1$-$C_2$ alcohol, dimethylsulfoxide, dimethylformamide, dichloromethane, or acetonitrile. Preferably, the second solvent includes, but is not limited to, at least one of ethylacetate, dimethylcarbonate, acetonitrile, toluene, methanol, dimethylsulfoxide, or dimethylformamide. Optionally the second solvent may include water. When the second solvent comprises two solvents, the ratio of solvents is about 90 to about 10 by volume. Preferably, the ratio of solvents is about 95 to about 5 by volume. More preferably, the second solvent is ethylacetate:methanol in a ratio of 95:5 by volume.

The second slurry may be carried out at a temperature of about −10° C. to about the reflux temperature of the second solvent.

After isolation, levalbuterol HCl Polymorph A may be dried, such as at room temperature and/or under reduced pressure. "Reduced pressure" refers to a pressure of less than one atmosphere, such as about 40 mm Hg to about 50 mm Hg.

The invention also encompasses a process for making pure levalbuterol HCl Polymorph A by the conversion of levalbuterol HCl Polymorph B into pure levalbuterol Polymorph A. The process comprises providing levalbuterol HCl Polymorph B, forming a slurry or suspension of levalbuterol HCl Polymorph B with an organic solvent mixture, and isolating pure levalbuterol Polymorph A from the slurry. The organic solvent includes, but is not limited to, at least one linear or branched $C_3$-$C_{10}$ ester, linear or branched $C_3$-$C_{10}$ ketone, linear or branched $C_3$-$C_{10}$ ether, $C_6$ to $C_{10}$ aromatic hydrocarbon, linear or branched $C_1$-$C_4$ alcohol, dimethylsulfoxide, dimethylformamide, methylene chloride, or acetonitrile. Optionally, the organic solvent includes water. Preferably, the organic solvent includes, but is not limited to, at least one of ethylacetate, tetrahydrofuran, dimethylcarbonate, acetonitrile, toluene, methanol, dimethylsulfoxide, or dimethylforamide. Typically, the temperature may be any suitable temperature wherein the conversion takes place, preferably the temperature is about 25° C. to 30° C., more preferably, the temperature is about room temperature.

Table 2 summarizes the loss on drying (LOD) as a weight percentage over a temperature range and water content for Polymorph A of levalbuterol.

TABLE 2

| Thermal Gravimetric Analysis (TGA) and Water Content for Sample Polymorphs. | | | | |
|---|---|---|---|---|
| | | TGA | | Water Content |
| Sample | Crystal Form | LOD (%) | Temp (° C.) | (%) |
| 1 | A | 0.30 | 27-102 | 0.36 |
| 2 | A | 0.30 | 46-102 | 0.45 |
| 4 | A | 0.28 | 33-131 | 0.29 |
| 7 | A | 0.09 | 38-133 | 0.16 |
| 10 | A | 1.17 | 50-102 | 0.30 |
| 14 | A | 0.03 | 53-153 | 0.09 |

Table 3 summarizes the hygroscopicity and crystal structure of a sample of levalbuterol HCl 100% Polymorph A after exposure to different levels of humidity for one week. After each exposure the water content was determined by Thermal Gravimetric Analysis (TGA) and reported as loss on drying (LOD) as a weight percentage. The crystal structure was determined by X-ray Diffraction (XRD). Based on the observations, after exposure of each sample to up to about 80% relative humidity, the water content of Polymorph A was determined to be only about 0.23 to 0.97 percent. After exposure of each sample at about 100% relative humidity for one week, the water content of Polymorph A was determined to be about 34 percent.

TABLE 3

| Results of hygroscopicity test of levalbuterol HCl Polymorph A | | |
|---|---|---|
| RH (%) | LOD (% [a] (Polymorph A) | Form by XRD[b] (Polymorph A) |
| 0 | 0.23 | A |
| 20 | 0.48 | A |
| 40 | 0.70 | A |
| 60 | 0.72 | A |
| 80 | 0.97 | A |
| 100 | 34.0 | A |

[a]The water content of each individual sample of Polymorph A after being exposed to the various levels of relative humidity (RH %) of column one, equilibrated and analyzed by thermal gravimetric analysis.
[b]The crystal structure of each individual sample of Polymorph A after being exposed to the various levels of relative humidity (RH %) of column one, equilibrated and analyzed by x-ray diffraction.

While the present invention is described with respect to particular examples and preferred embodiments, it is understood that the present invention is not limited to these examples and embodiments. The present invention, as claimed, therefore includes variations from the particular examples and preferred embodiments described herein, as will be apparent to one of skill in the art.

EXAMPLES

The X-Ray diffraction (XRD) analysis was conducted using an ARL X-Ray powder diffractometer (model X'TRA-030) equipped with a Peltier detector, round standard aluminum sample holder with round zero background, and quartz plate. The scanning parameters were from a range of about 2-40 degree two θ (±0.2 degrees) and a continuous scan at a rate of about 3 degrees/min. One of ordinary skill in the art understands that experimental differences may arise due to differences in instrumentation, sample preparation, or other factors.

Fourier transform infrared (FT-IR) spectroscopy was conducted using a Perkin-Elmer Spectrum 1000 Spectrometer at about 4 $cm^{-1}$ resolution with about 16 scans in the range of 4000-400 $cm^{-1}$. Samples were analyzed in KBr pellet and the instrument was calibrated using an empty cell as a background.

Differential scanning calorimetry (DSC) was conducted using a Mettler Toledo DSC $822^e$/700 with a sample weight of about 3-5 mg, a heating rate of about 10° C./min., using a 3 holed crucible, under a stream of $N_2$ at a flow rate of about 40 ml/min. The sample was scanned between a range of about 30° C. to about 250° C. at a heating rate of about 10° C./minute.

Thermal Gravimetric Analysis (TGA) was conducted using a Mettler Toledo TGA/SDTA $851^e$ using a sample weight of about 7-15 mg, a heating rate of about 10° C./min. under a $N_2$ stream at a $N_2$ flow rate of about 50 ml/min. The samples were scanned at a range between about 30° C. to about 250° C.

The HPLC analysis was conducted using a column POLARIS C18-A 250 mm×4.6 mm×5.0 mm (cat n. 2002-250x046) and a mobile phase. The mobile phase comprised a gradient of phosphate buffer at about pH 3.00 and acetonitrile. The eluent flow was about 1.0 ml/min. An HP 1100 HPLC Hewlett Packard VWD detector was set to a wavelength of about 230 nm.

Example 1

In a 500 ml reactor equipped with a condenser, thermometer, and mechanical stirrer loaded at room temperature and under nitrogen a suspension of wet pure (R)-SLB.(D)-DBTA (30 g wet, 25.4 g at 100%; 0.0425 moles) in acetonitrile (300 ml) was formed. The suspension was cooled to 0° C.±2° C., the temperature was maintained, and in about 5 minutes HCl (37%, 5.0 g, 0.051 moles, 1.2 eq.) was added. The suspension was stirred at 0° C.±2° C. for 1 hour; the solid was collected by filtration and washed with acetonitrile (3×16 ml). The wet solid (15.1 g) was suspended in an ethylacetate and methanol mixture (75 ml, 90:10 v/v), and the suspension was stirred at 20° C. to 25° C. for 4 hrs. The solid was collected by filtration and washed with ethylacetate to obtain levalbuterol HCl Polymorph A (11 g dry weight, 95%).

Example 2

In a 1000 ml reactor equipped with a condenser, thermometer, and mechanical stirrer loaded at room temperature and under nitrogen a suspension of wet pure (R)-SLB.(D)-DBTA (93.96 g, 70 g at 100%, 0.117 moles) in ethylacetate (729 ml) and methanol (84 ml) was formed. The suspension was cooled to 0° C.±2° C., maintained at the temperature, and in about 2 minutes HCl (37.3%, 13.73 g, 0.14 moles, 1.2 eq.) was added. The suspension was stirred at 0° C.±2° C. for 1 hour, and then the solid was collected by filtration and washed with ethylacetate (2×55 ml). The solid was dried at 22° C.±2° C. under vacuum (40 to 45 mm Hg) for 20 hours to obtain levalbuterol HCl Polymorph A (32 g dry weight).

Example 3

In a 500 ml reactor equipped with a condenser, thermometer, and mechanical stirrer loaded at room temperature and under nitrogen a suspension of wet pure (R)-SLB.(D)-DBTA (26.5 g wet, 20 g at 100%, 0.033 moles) in ethylacetate (233 ml) was formed. The suspension was cooled to 0° C.±2° C. and maintained at that temperature, and in about 2 minutes a solution of HCl (37.3%, 3.93 g, 0.04 moles, 1.2 eq.) was added. The suspension was stirred at 0° C.±2° C. for 1 hour;

the solid collected by filtration and washed with ethylacetate (2×17.5 ml). The wet product (9.3 g) was dried at 22° C.±2° C. under vacuum (40 to 45 mm Hg) for 20 hours to obtain levalbuterol Polymorph A (9 g dry weight.

Example 4

In a 500 ml reactor equipped with a condenser, thermometer, and mechanical stirrer loaded at room temperature and under nitrogen a suspension of wet pure (R)-SLB.(D)-DBTA (30 g wet, 25.4 g at 100%, 0.0425 moles), ethylacetate (243 ml), and DMF (26.9 ml) was formed. The suspension was cooled to 0° C.±2° C., maintained at the temperature, and in about 5 minutes HCl (37%, 4.54 g, 0.046 moles, 1.1 eq.) was added. The suspension was stirred at 0° C.±2° C. for 1 hour; the solid was collected by filtration, and washed with ethylacetate-DMF (90:10).

The wet product (15.5 g) was suspended in a mixture of ethylacetate and methanol (75 ml, 90:10 v/v). The suspension was stirred at 20° C. to 25° C. for four hours and a solid was collected by filtration. The solid was washed with ethylacetate, dried at 22° C.±2° C. under vacuum (40 to 45 mm Hg) for 20 hours to obtain levalbuterol Polymorph A (11 g dry weight, 93.9% yield).

Example 5

In a 500 ml reactor equipped with a condenser, thermometer, and mechanical stirrer loaded at room temperature and under nitrogen a suspension of wet pure (R)-SLB.(D)-DBTA (39.73 g wet, 30 g at 100%; 0.05 moles), in ethylacetate (331 ml) and MeOH (18 ml) was formed. The suspension was cooled to 0° C.±2° C., the temperature was maintained, and in about 5 minutes HCl (37%, 5.89 g, 0.06 moles, 1.2 eq.) was added. The suspension was stirred at 0° C.±2° C. for 1 hour, the solid was collected by filtration, and washed with ethylacetate (3×16 ml). The wet solid (18.1 g) was suspended in an ethylacetate and methanol mixture (90 ml, 90:10 v/v) and the suspension was stirred at 20° C. to 25° C. for 4 hrs. The solid was collected by filtration and washed with ethylacetate to obtain levalbuterol HCl Polymorph A (12.9 g dry weight, 94%) in 99.9% purity as determined by HPLC (any impurity <0.1%).

Example 6

In a 500 ml reactor equipped with a condenser, thermometer, and mechanical stirrer loaded at room temperature and under nitrogen a suspension of wet pure (R)-SLB.(D)-DBTA (30 g, 25.4 g at 100%, 0.0425 moles) in acetonitrile (300 ml) was formed. The suspension was cooled to 0° C.±2° C., maintained at the temperature, and in about 5 minutes HCl (37%, 5.0 g, 0.051 moles, 1.2 eq.) was added. The suspension was stirred at 0° C.±2° C. for 1 hour, and then the solid was collected by filtration, which was washed with acetonitrile (3×16 ml). The wet solid (15.1 g) was suspended in a mixture of ethylacetate and methanol (75 ml, 90:10 v/v), and the suspension was stirred at 20° C. to 25° C. for 4 hrs. The solid was collected by filtration and washed with ethylacetate to obtain levalbuterol HCl Polymorph A (11 g dry weight, 95%) in 99.8% purity as determined by HPLC (any impurity <0.1%).

Example 7

In a 100 ml reactor equipped with a condenser, thermometer, and mechanical stirrer loaded at room temperature and under nitrogen a suspension of wet pure (R)-SLB.(D)-DBTA (8 g, 0.013 moles, 1 eq.) and isopropanol (40 ml). The suspension was cooled at 15° C. to 20° C. and HCl in methanol (31.2%, 1.82 g, 0.016 moles, 1.16 eq.) was added. The suspension was stirred at room temperature, cooled to 0° C. to 2° C. for 1 hour, the solid was collected by filtration, and washed with isopropanol (5 ml) and then ethylacetate (2×5 ml). After drying, levalbuterol Polymorph A was collected (3 g).

Example 8

In a 50 ml reactor equipped with a condenser, thermometer, and mechanical stirrer loaded at room temperature and under nitrogen a suspension of wet pure (R)-LVL.HCl Polymorph B (8 g), ethylacetate (36 ml), and methanol (4 ml) was formed. The suspension was stirred at 23° C. to 24° C. and a sample was taken at time intervals of 4 hours, 8 hours, 20 hours, and 24 hours. Each sample taken was cooled to 0° C. to 2° C. for 1 hour, filtered, and the solid collected was washed with isopropanol (5 ml) followed by ethylacetate (2×5 ml). The samples were dried and analyzed by FT-IR spectroscopy and X-ray diffraction to detect the presence of levalbuterol HCl Polymorph A.

Example 9

In a 500 ml reactor equipped with a condenser, thermometer, and mechanical stirrer loaded at room temperature and under nitrogen a suspension of wet pure (R)-SLB.(D)-DBTA (30 g wet, 25.4 g at 100%, 0.0425 moles), ethylacetate (243 ml) and DMF (26.9 ml). The suspension was cooled at 0° C.±2° C., the temperature was maintained, and in about 5 minutes HCl (37%, 4.54 g, 0.046 moles, 1.1 eq.). The suspension was stirred at 0° C.±2° C. for 1 hour, the solid was collected by filtration, and washed with ethylacetate-DMF (90:10) and then with ethylacetate. The wet solid (15.5 g) was suspended in a mixture of ethylacetate and methanol (75 ml, 90:10 v/v). The suspension was stirred at 20° C. to 25° C. for 4 hrs, the solid was collected by filtration and washed with ethylacetate. Levalbuterol Polymorph A was collected (11 g, dry weight, 93.9%) in 99.7% purity as determined by HPLC (any impurity <0.1%).

Example 10

Prior art examples were repeated, which results are summarized in Table 4. In particular, Example 18 and Example 19 of Chinese patent No. 1273966 and Example 7 of WO 95/32178 was repeated.

TABLE 4

Results of Prior Art Examples

| Examp No. | Solvent/Temp/ Time | Conditions | Xtal Form |
|---|---|---|---|
| 11[a] | Lvl base in EtOH + HCl in $Et_2O$ + $Et_2O$ | According to CN 1273966 example 18 | A |
| 12[b] | Xtl. No. 11 from EtOH-MTBE | According to CN 1273966 example 18 | A |
| 13[a] | Lvl base in EtOH + HCl in $Et_2O$ + MTBE | According to WO 95/32178 example 7 | A |
| 14[b] | Xtl. No. 13 from EtOH-MTBE | According to WO 95/32178 example 7 | A |
| 15[a] | R-SLB.DBTA + Acetone + HCl in $Et_2O$ | According to CN 1273966 example 19 | A > B |

TABLE 4-continued

Results of Prior Art Examples

| Examp No. | Solvent/Temp/ Time | Conditions | Xtal Form |
|---|---|---|---|
| [b] | Xtl. No. 15 from EtOH-MTBE | According to CN 1273966 example 19 | A |

[a]The stating material was a crude sample of levalbuterol base.
[b]The starting material was a purified sample of levalbuterol HCl of the prior example.

Example 13

Repetition of Example 7 of WO95/321198

In a 50 ml reactor equipped with a condenser, thermometer, and mechanical stirrer loaded at room temperature levalbuterol free base (3.2 g wet, 3 g at 100%) and absolute ethanol (12.5 ml). The solution was cooled at 0° C. to 5° C. and ethereal HCl 1.0 N (12 ml) was added. The suspension was warmed to room temperature and after 30 min MTBE (12.5 ml) was added. After an additional 30 min at room temperature, the suspension was cooled at 0° C. to 5° C. and after 2 hours, the solid was collected by filtration and washed with MTBE (3 ml) to obtain levalbuterol Polymorph A (1.75 g).

Example 14

Recrystallization of the Example 13 Product

In a 25 ml reactor equipped with a condenser, thermometer, and mechanical stirrer loaded at room temperature levalbuterol HCl (1 g) and absolute ethanol (19 ml). The solution was warmed to 45° C. to 50° C. to obtain a solution. The solution was cooled to room temperature and after MTBE (9.5 ml) was added. The solution was stirred at room temperature for 1 hour to obtain a suspension. The solid was collected by filtration and washed with MTBE (3 ml) to obtain levalbuterol Polymorph A (0.6 g).

Example 15

Repetition of Example 19 of CN 1273966

In a 100 ml reactor equipped with a condenser, thermometer, and mechanical stirrer loaded at room temperature and under nitrogen a suspension of wet pure (R)-SLB(D)-DBTA (5 g) and acetone (50 ml). The suspension was cooled at 30° C. and HCl ethereal solution 1.56 N (14 ml) and ether (50 ml) was added. The suspension was stirred at room temperature for 15 min, the solid was collected by filtration and washed with ether (5 ml) to obtain a mixture of levalbuterol Polymorph A>Polymorph B (1.9 g).

Example 16

Recrystallization of the Example 15 Product

In a 25 ml reactor equipped with a condenser, thermometer, and mechanical stirrer loaded at room temperature levalbuterol HCl (1.2 g) and absolute ethanol (15 ml). The solution was warmed to 45° C. to 50° to obtain a solution. The solution was cooled to room temperature and after MTBE (8.75 ml) was added. The solution was stirred at 15° C. for 2 hours to obtain a suspension. The solid was collected by filtration and washed with MTBE (3 ml) to obtain levalbuterol Polymorph A (0.8 g).

Example 17

Standard Reaction

In a 2000 ml reactor equipped with a condenser, thermometer, and mechanical stirrer loaded at room temperature and under nitrogen a suspension of wet pure (R)-SLB.(D)-DBTA (112 g wet, 100 g at 100%, 0.1673 moles), ethylacetate (1127 ml) and methanol (60 ml) was formed. The suspension was cooled at 0 E ±2° C., the temperature was maintained, and in about 12 minutes HCl (37%, 19.8 g, 0.2007 moles, 1.2 eq.) was added. The suspension was stirred at 0EC ±2° C. for 1 hour, the solid was collected by filtration, and washed with ethylacetate-methanol (95:5, 50 ml) and then with ethylacetate alone (2×50 ml).

The wet solid (59.6 g) was suspended in a mixture of ethylacetate and methanol (99 ml, 90:10 v/v). The suspension was stirred at 10 EC for 4 hrs, the solid was collected by filtration and washed with a mixture of ethylacetate and methanol (90:10) and then ethylacetate (2×20 ml). Levalbuterol Polymorph A was collected (14.67 g, dry weight) in 99.73% purity as determined by HPLC.

What is claimed is:

1. A process for making levalbuterol HCl Polymorph A comprising:

suspending or forming a first slurry of the R enantiomer of albuterol D-dibenzoyl tartrate complex in at least a first organic solvent;

adding HCl to the suspension or slurry of the solid R enantiomer of albuterol D-dibenzoyl tartrate complex until the pure levalbuterol HCl Polymorph A is formed; and isolating the pure levalbuterol HCl Polymorph A;

wherein said levalbuterol HCl Polymorph A is characterized by an X-ray diffraction pattern containing peaks at 10.7, 15.3, 15.6, 19.1 and 23.9 degree two-theta±0.2 degree two-theta.

2. The process according to claim 1, wherein the first organic solvent is at least one linear or branched $C_3$-$C_{10}$ ester, linear or branched $C_3$-$C_{10}$ ketone, linear or branched $C_3$-$C_{10}$ ether, aromatic hydrocarbon, linear or branched $C_1$-$C_4$ alcohol, dimethylsulfoxide, dimethylformamide, methylene chloride, or acetonitrile.

3. The process according to claim 1, wherein the first solvent is at least one of ethylacetate, tetrahydrofuran, dimethylcarbonate, acetonitrile, toluene, methanol, dimethylsulfoxide, or dimethylforamide.

4. The process according to claim 2, wherein the aromatic hydrocarbon is $C_6$ to $C_{10}$.

5. The process according to claim 1, wherein the first solvent comprises two solvents.

6. The process according to claim 5, wherein the two solvents comprise one solvent that is present in about 70% and a second solvent that is present in about 30% by volume.

7. The process according to claim 5, wherein the first solvent comprises ethylacetate present in about 70% to 100% and methanol present in about 1% to 30% by volume.

8. The process according to claim 7, wherein the first solvent comprises ethylacetate present in 95% and methanol present in about 5% by volume.

9. The process according to claim 1, wherein the HCl is at least one of aqueous HCl (37%), HCl gas, HCl in DMF, or HCl in ether.

10. The process according to claim 1, further comprising suspending or forming a second slurry of the pure levalbuterol HCl Polymorph A in a second solvent; and isolating the pure levalbuterol HCl Polymorph A.

11. The process according to claim 10, wherein the, second solvent is at least one $C_3$-$C_5$ ester, $C_6$-$C_7$ aromatic hydrocarbon, $C_1$-$C_2$ alcohol, dimethylsulfoxide, dimethylformamide, dichloromethane, or acetonitrile.

12. The process according to claim 11, wherein the second solvent is at least one of ethyl acetate, dimethylcarbonate, acetonitrile, toluene, methanol, dimethylsulfoxide, or dimethylformamide.

* * * * *